United States Patent [19]

Honda et al.

[11] Patent Number: 5,054,948
[45] Date of Patent: Oct. 8, 1991

[54] LIQUID APPLICATOR

[75] Inventors: Shinzo Honda, Tokyo; Kazunori Hirose; Zensho Kanda, both of Yamanashi, all of Japan

[73] Assignee: Terumo Kabushiki Kaisha, Tokyo, Japan

[21] Appl. No.: 559,643

[22] Filed: Jul. 30, 1990

[30] Foreign Application Priority Data

Aug. 1, 1989 [JP] Japan .................................. 1-199591
Aug. 1, 1989 [JP] Japan .................................. 1-199592

[51] Int. Cl.$^5$ ............................................ A47L 13/17
[52] U.S. Cl. .................................... 401/196; 401/198; 401/202
[58] Field of Search ........................ 401/196, 198, 202

[56] References Cited

U.S. PATENT DOCUMENTS

| | | | |
|---|---|---|---|
| 1,363,960 | 12/1920 | Davis | 401/265 X |
| 2,676,349 | 4/1954 | Vosburg | 401/202 X |
| 3,369,543 | 2/1968 | Ronco | 401/202 X |
| 3,618,604 | 11/1971 | Ness . | |
| 4,282,986 | 8/1981 | Ekenstam et al. . | |
| 4,415,288 | 11/1983 | Gordon et al. . | |
| 4,733,586 | 3/1988 | Manusch | 401/199 |

FOREIGN PATENT DOCUMENTS

| | | |
|---|---|---|
| 73799/87 | 6/1987 | Australia . |
| 28001/89 | 7/1988 | Australia . |
| 63-181775 | 7/1988 | Japan . |
| 63-181776 | 7/1988 | Japan . |
| WO85/03275 | 8/1985 | PCT Int'l Appl. . |
| WO89/05695 | 6/1989 | PCT Int'l Appl. . |

Primary Examiner—Robert A. Hafer
Assistant Examiner—Kerry Owens
Attorney, Agent, or Firm—Frishauf, Holtz, Goodman, & Woodward

[57] ABSTRACT

A liquid applicator includes a case for containing a liquid and an applying member, housed in the case, for applying the liquid. The case is broken to expose the applying member, thereby allowing application of the liquid via the applying member. The shape of the distal end face of the applying member is formed to be substantially rhombic or elliptic so that the thickness in one direction is larger than the thickness in another direction perpendicular to the one direction. By moving the distal end face of the applying member in the another direction perpendicular to the one direction, the liquid can be applied on a wide affected part within a short time period.

21 Claims, 6 Drawing Sheets

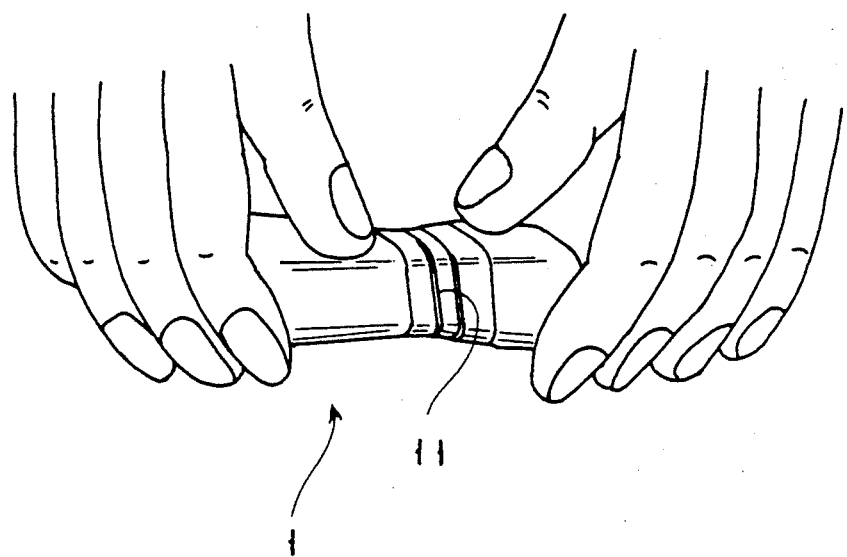
F I G. 12
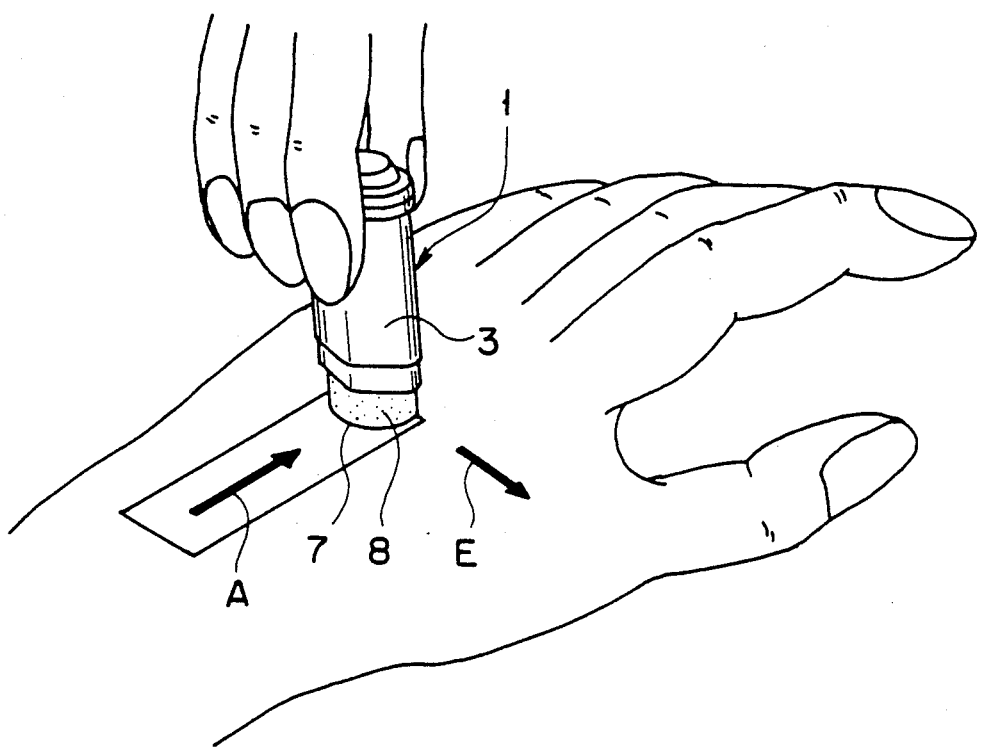
F I G. 13

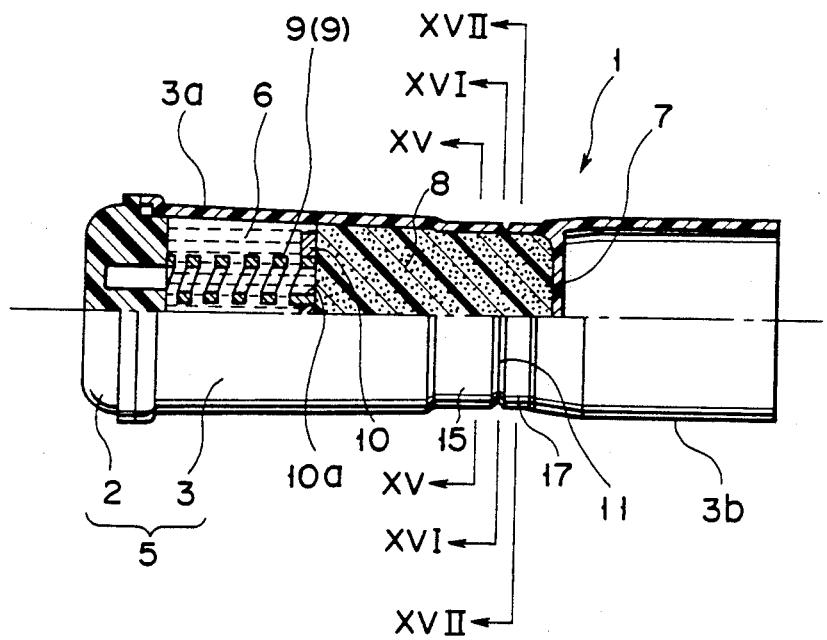
FIG. 14
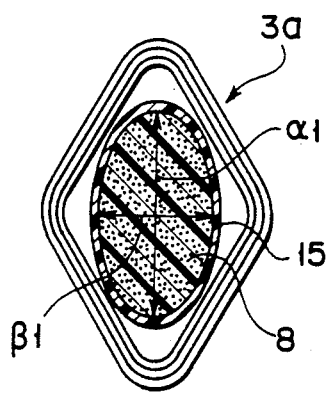 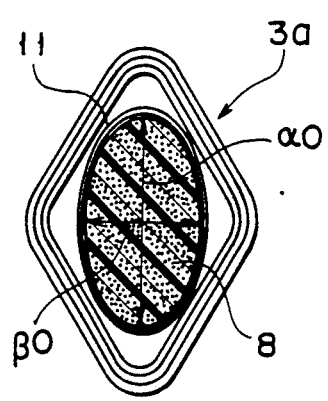 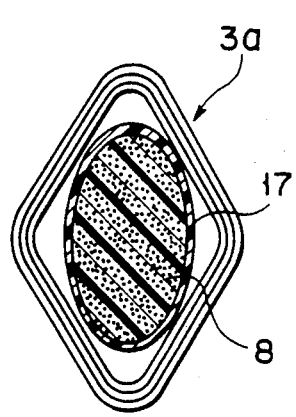
FIG. 15  FIG. 16  FIG. 17

LIQUID APPLICATOR

BACKGROUND OF THE INVENTION

1. Field of the Invention

The present invention relates to a liquid applicator having a case for containing a liquid such as a disinfectant solution and an applying member, housed in the case, for applying the liquid, which can be carried out in fields or kept in a house for a sudden need and which can apply a liquid such as a disinfectant solution on an affected part by opening the case.

2. Description of the Related Art

Generally, as a disinfecting/curing means for use in the case of an emergency such as an external wound or the sting of an insect or for use in a house, a liquid such as a disinfectant solution contained in a medicine bottle is impregnated in an applying member such as absorbent cotton, and the applying member is used to clean an affected part or apply the solution on the affected part.

Examples of a conventional simple liquid applicator which can eliminate cumbersome handling are an applicator having an applying member with liquid permeable properties at an opening of a case of a liquid such as a disinfectant solution, for directly applying the liquid on an affected part by using the applying member, an applicator having a mechanism for spraying a liquid, and an applicator which seals a napkin-like applying member consisting of a non-woven fabric and containing a liquid.

In recent years, a liquid applicator 50 as shown in FIG. 1 is proposed as a sanitary liquid applicator which can be easily handled by combining advantages of the above conventional applicators (Published Unexamined Japanese Patent Application No. 63-181776). This liquid applicator 50 seals a liquid 54 such as a disinfectant solution in an amount which can be consumed at once in a case 52. The case 52 is constituted by a plunger portion 56 and a case main body 58 which are connected at an opening end 62 of the case main body 58. The case main body 58 is constituted by a large-diameter portion 58a and a small-diameter portion 58b continuous with each other. An opening means 64 is formed in the small diameter portion 58b (FIG. 1). In order to use this liquid applicator 50, the opening means 64 of the case 52 is opened (FIG. 2), and the liquid 54 such as a disinfectant solution is directly applied on an affected part by an exposed columnar applying member 66 (FIG. 3.)

In addition, a liquid applicator 70 as shown in FIG. 4 is provided by the present assignee (Japanese Patent Application No. 01-30572). This liquid applicator 70 is formed to be substantially the same as the liquid applicator 50 shown in FIG. 1 except that a columnar applying member 86 is elongated. A case 72 is constituted by a plunger portion 76 and a case main body 78 which are connected at an opening end 82 and seals a liquid such as a disinfectant solution.

A reinforcing core member 92 is inserted in the applying member 86 to support the elongated applying member 86. The reinforcing core member 92 has elasticity which allows the member 92 to be bent when the case 72 is opened and has rigidity which allows the member 92 to support the applying member 86 when a side applying portion 94 of the applying member 86 is used to apply the liquid on an affected part.

In order to use the liquid applicator 70, an opening means 84 of the case 72 is opened (FIG. 5), and the liquid is applied by the applying portion 94 of the exposed applying member 86 on an affected part (FIG. 6). Therefore, the liquid can be applied on a wide area of the affected part by one application action.

In the above liquid applicator 50, however, the columnar applying member 66 is obtained by binding a large number of long acetylcellulose-based fibers to form a columnar member as a whole or by using a porous material such as sponge. Therefore, the columnar applying member 66 does not have satisfactory rigidity, and it is difficult to elongate its exposed portion. As a result, since the distal end face of the applying member is mainly used as an applying portion, it takes a long time to apply the liquid on a wide affected part, as shown in FIG. 3. Although the diameter of the columnar applying member 66 can be increased to apply the liquid on a wide affected part within a short time period, the entire applicator size is increased upon increasing the diameter of the case 58. Therefore, the applicator cannot be conveniently kept in a house or be carried out.

The prior art liquid applicator 70 discussed above can apply a liquid on a wide area of an affected part by one application action. However, the structure of this applicator is comparatively complicated, or its entire length is increased since the applying member 86 is elongated.

SUMMARY OF THE INVENTION

The present invention, therefore, has been made in consideration of the above situation and has as its object to provide a liquid applicator which has a simple structure and a length substantially the same as that of a conventional applicator and can apply a liquid on a wide affected part within a short time period without causing adhesion of the liquid on fingers after it is opened.

In order to achieve the above object, a liquid applicator of the present invention comprises a case for containing a liquid, and an applying member, housed in the case, for applying the liquid, the case exposing the applying member when broken, thereby allowing application of the liquid. The shape of the distal end face of the applying member is formed such that the thickness in one direction is larger than the thickness in another direction perpendicular to the one direction.

In a preferred embodiment, a ratio of the thickness in the one direction to the thickness in the another direction perpendicular to the one direction is about 3 to 1.2. The shape of the distal end face is, e.g., substantially a rhombus or ellipse. The cross section of the opening means formed in the broken portion of the case may be an ellipse substantially the same as the shape of the distal end face of the applying member.

According to the liquid applicator having the above arrangement, at least the shape of the distal end face of the applying member for applying a liquid on an affected part is formed such that the thickness in the one direction of the distal end face is larger than that in the another direction perpendicular to the one direction. Therefore, when a portion of the case is broken to open the case and expose the applying member, a liquid can be applied on a wide affected part within a short time period by moving the distal end face of the applying member in a direction perpendicular to the direction of the larger thickness. That is, although the liquid applicator of the present invention has a simple structure and an entire axial length substantially the same as that of a conventional applicator, it can apply a liquid on a wide affected part within a short time period without causing adhesion of the liquid on fingers after it is opened.

Additional objects and advantages of the invention will be set forth in the description which follows, and in part will be obvious from the description, or may be learned by practice of the invention.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 12 is a perspective view for explaining an opening state of the liquid applicator shown in FIG. 7;

FIG. 13 is a perspective view for explaining an application state of the applicator shown in FIG. 7;

FIG. 14 is a partially cutaway longitudinal sectional view showing a liquid applicator according to the second embodiment of the present invention; and FIGS. 15 to 17 are side views taken along lines XV—XV, XVI—XVI, and XVII—XVII shown in FIG. 14, respectively.

DETAILED DESCRIPTION OF THE PREFERRED EMBODIMENTS

Figure 1:
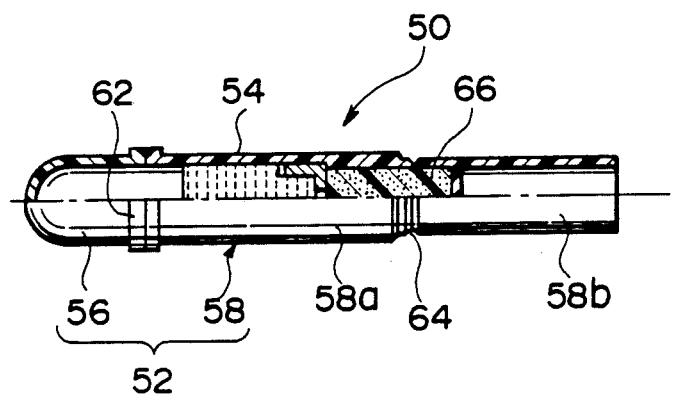
FIG. 1 is a partially cutaway longitudinal sectional view showing a conventional liquid applicator.
Figure 2:
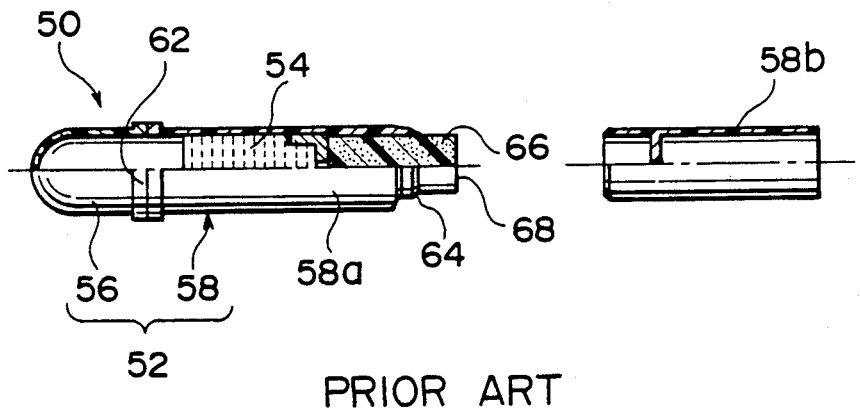
FIG. 2 is a partially cutaway longitudinal sectional view showing a state in which the applicator shown in FIG. 1 is opened.
Figure 3:
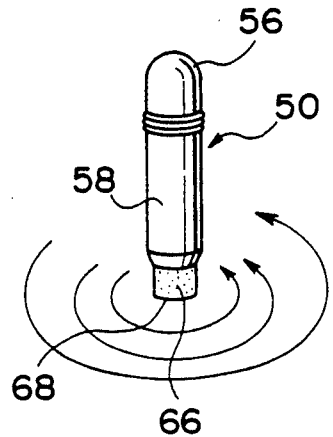
FIG. 3 is a perspective view for explaining an application state of the applicator shown in FIG. 1.
Figure 4:
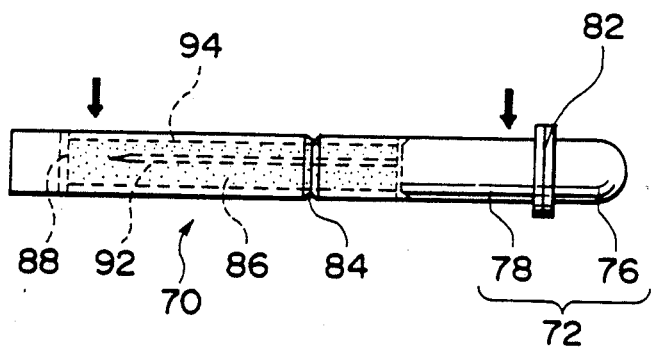
FIG. 4 is a partially cutaway longitudinal sectional view showing another conventional liquid applicator.
Figure 5:
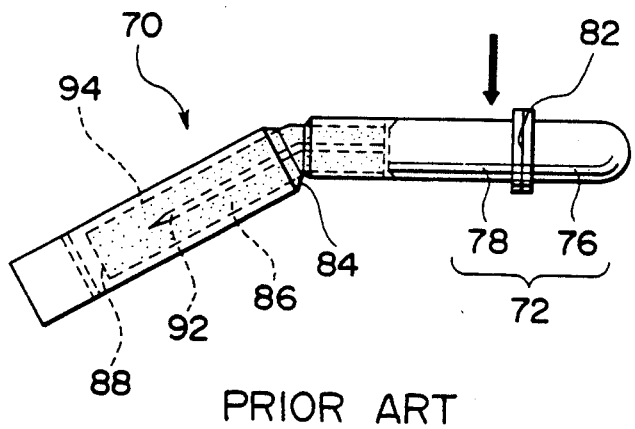
FIG. 5 is a partially cutaway longitudinal sectional view showing a state in which the applicator shown in FIG. 4 is opened.
Figure 6:
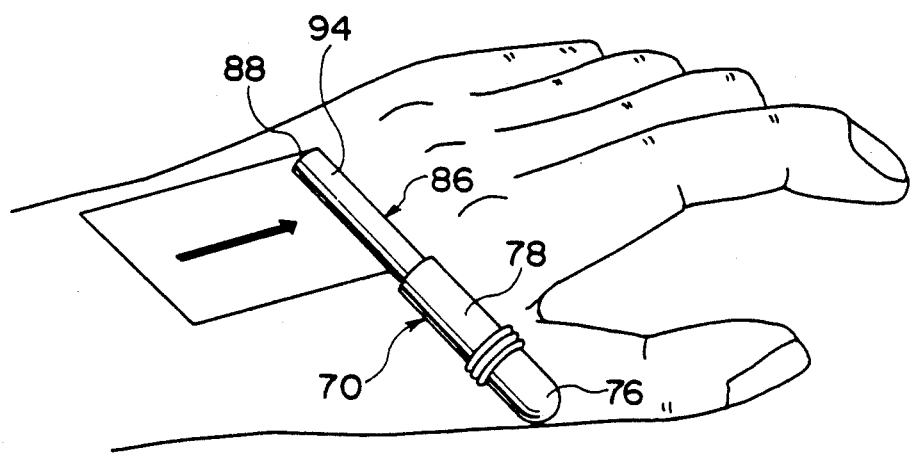
FIG. 6 is a perspective view for explaining an application state of the applicator shown in FIG. 4.
Figure 7:
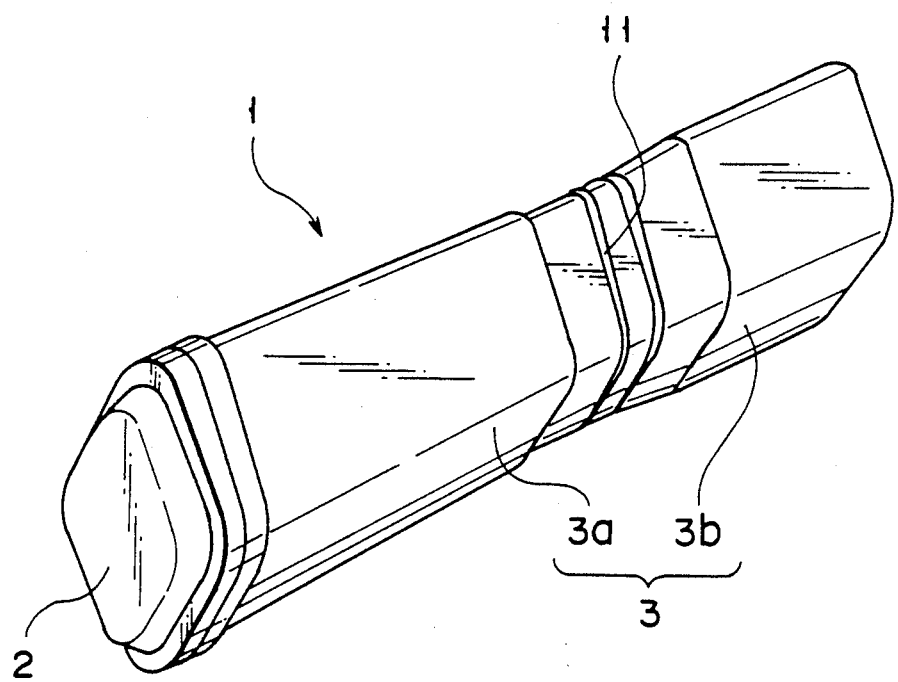
FIG. 7 is a perspective view showing a liquid applicator according to the first embodiment of the present invention.

A liquid applicator 1 comprises a case 5 constituted by a cap portion 2 consisting essentially of a hard plastic material and having a substantially rhombic cross section and a case main body 3 consisting essentially of a hard plastic material and having a substantially rhombic cross section. The cap portion 2 and the case main body 3 are connected at an opening end 4 of the case main body 3. A substantially rhombic applying member (to be simply referred to as an applying member hereinafter) 8 for applying a liquid 6 such as a disinfectant solution contained in the case 5 is housed in the case 5. Urging springs 9 are fixed to the cap portion 2, and a rhombic plate 10 is fixed to the distal ends of the springs 9. A hole 10a is formed in the plate 10. The case main body 3 comprises by a tapered cylindrical portion 3a having an inclined wall surface and a straight cylindrical portion 3b. An opening means 11 (i.e., a separable connecting means) having a thin circumferential wall is formed at a portion of the case main body 3.

Figure 8:
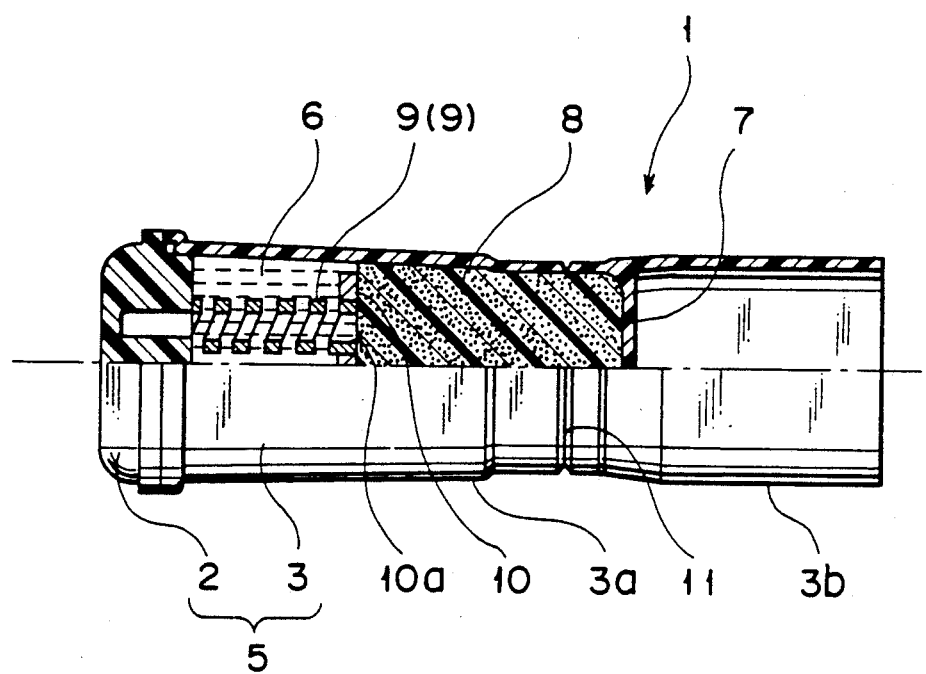
FIG. 8 is a partially cutaway longitudinal sectional view showing the liquid applicator shown in FIG. 7.

The liquid 6 such as a disinfectant solution is sealed in a hollow portion of the tapered cylindrical portion 3a as shown in FIG. 8. The applying member 8 is housed in the hollow portion of the tapered cylindrical portion 3a of the case main body 3 molded into a rhombic shape as shown in FIG. 8. That is, the circumferential surface of the applying member 8 is held by the inclined wall surface of the tapered cylindrical portion 3a, and its proximal end portion is supported by the rhombic plate 10.

Figure 10:
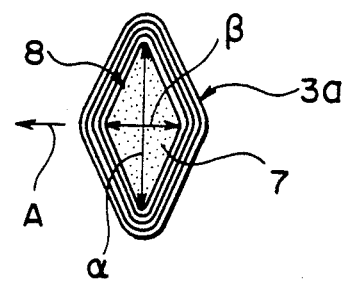
FIG. 10 is a side view taken along a line X—X in FIG. 9.

Since the hole 10a for passing the liquid 6 is formed in the rhombic plate 10, the liquid 6 is smoothly supplied to the applying member 8. In addition, since the application pressure of the applying member 8 can be kept at a predetermined pressure by the urging springs 9 upon application of the liquid 6 on an affected part, the liquid 6 is not excessively applied on the affected part. Furthermore, since the applying member 8 has a substantially rhombic shape, a thickness in one direction, e.g., $\alpha$ shown in FIG. 10 is larger than a thickness in a direction perpendicular to the first direction, e.g., $\beta$ shown in FIG. 10. Therefore, when the applying member 8 is moved in a direction indicated by an arrow A in FIG. 10, the liquid 6 can be applied on a wide area of an affected part by one application action. A ratio of $\alpha$ to $\beta$ ($\alpha/\beta$) is preferably 3 to 1.2. If the ratio exceeds 3, the opening means 11 cannot be easily opened. If the ratio does not reach 1.2, an application area is undesirably decreased.

The cap portion 2 and the case main body 3 consist essentially of a hard plastic material which is inactive, i.e., does not dissolve, is not denatured and does not swell, and less permeable with respect to the liquid 6. The cap portion 2 and the case main body 3 preferably consist essentially of the same type of hard plastic material in order to perform ultrasonic fusing. Therefore, a homopolymer of polypropyrene is preferably used as the hard plastic material to mold each part by injection molding, extrusion molding, blow molding, injection-blow molding, or vacuum molding. Note that the case main body 3 and the cap portion 2 must be strongly connected to form the case 5 while the liquid 6 is contained in the hollow portion of the tapered cylindrical portion 3a. When the same type of hard plastic material is used, ultrasonic fusing can be performed to strongly connect these parts.

Figure 11:
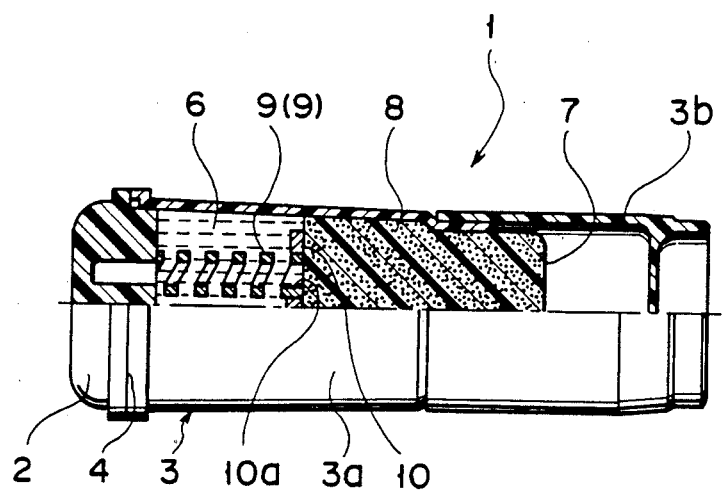
FIG. 11 is a partially cutaway sectional view showing a state in which a straight cylindrical portion of the case main body of the applicator shown in FIG. 7 is used as a cap.

The opening means 11 (i.e., a separable connecting means) is formed in the straight cylindrical portion 3b located at a side opposite to the cap portion 2 from substantially the middle point in the entire longitudinal direction of the case main body 3 of the case 5. This thickness of the circumferential wall of this opening means 11 is decreased to be 0.05 to 0.5 mm, and preferably, 0.1 to 0.2 mm. The opening means 11 is, e.g., a V-shaped groove as shown in FIG. 11, and the radius of curvature of the groove bottom is minimized. It is important to form the opening means 11 such that the opening means 11 does not easily receive a force in a normal state but can be easily broken upon concentration of a stress on the groove bottom only when a force in a breaking direction is applied sideward on the case main body 3.

Figure 9:
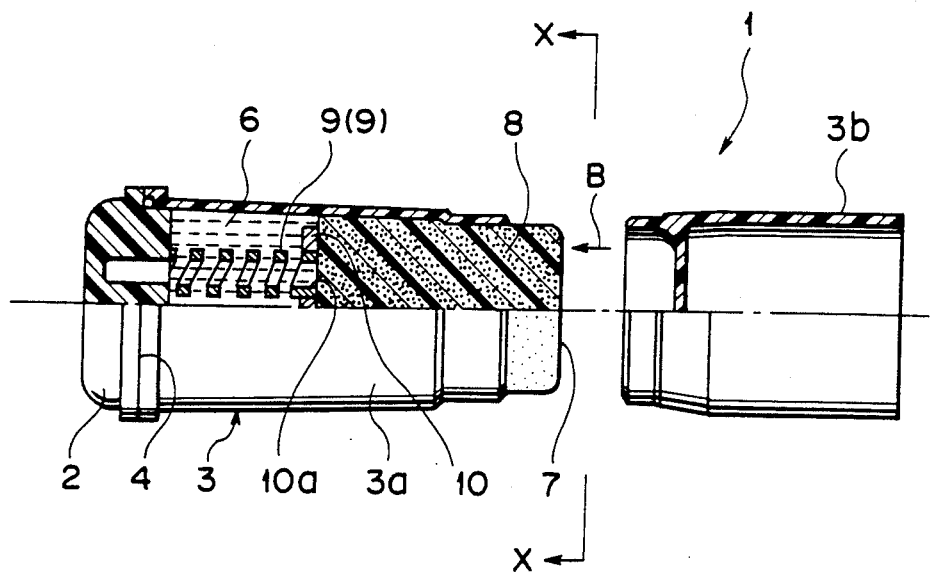
FIG. 9 is a partially cutaway longitudinal sectional view showing a state in which a case main body of the liquid applicator is opened.

In order to open the case 5, a user holds both sides of the opening means 11 with both hands, puts the thumbs of both hands at both sides of the opening means 11, and applies a force in the bending direction on the case main body 3, thereby breaking the opening means 11. As a result, the case main body 3 of the case is separated into the tapered cylindrical portion 3a and the straight cylindrical portion 3b, and the applying member 8 is exposed from the distal end of the tapered cylindrical portion 3a as shown in FIG. 9. That is, the applying member 8 is located at the tapered cylindrical portion 3a side, and its distal end face 7 is exposed by about 3 to 5 mm from the opening means 11. Therefore, when the substantially rhombic distal end face of the applying member 8 is moved in the direction indicated by an arrow A shown in FIG. 10, the liquid 6 can be easily applied or dropped to clean a wide affected part within a short time period.

The applying member 8 preferably consists essentially of a material which has excellent permeability to the liquid 6, is inactive with respect to the liquid 6, has an excellent form retention property, provides a good feeling when the liquid is applied on a skin, and hardly produces pieces of the applying member. Examples of the material of the applying member 8 are a material obtained by binding a large number of long acetylcellulose-based fibers to form an elliptic column as a whole and a porous material.

In the tapered cylindrical portion 3a released from a sealed state upon opening of the opening means 11, when a force in a direction indicated by an arrow B shown in FIG. 9 is applied on the applying member 8 of the liquid applicator 1, i.e., when the applying member 8 is set in an application state, it is compressed between an object to be applied (e.g., the back of hand) and the rhombic plate 10. A liquid portion passing through the hole 10a of the plate 10 soaks in the applying member 8 by a capillary action. Therefore, when the applying member 8 is compressed, the liquid 6 leaks from the distal end face 7 of the applying member 8 and is applied or dropped to clean a necessary portion.

The liquid applicator 1 of the present invention is assembled as follows. That is, the applying member 8 is inserted from the opening end 4 side into the case main body 3, the liquid 6 is contained therein, and the cap portion 2 is connected at a flange portion of the opening end 4 by ultrasonic fusing, in which the cap has the urging springs 9 with the rhombic plate 10 fixed to their distal ends.

An operation of the liquid applicator 1 having the above arrangement will be described below. Since the cap portion 2 and the case main body 3 of the liquid applicator 1 consist essentially of a hard plastic material, the cap portion 2 and the case main body 3 serve as holding portions of the applying member 8 when the applicator 1 is used. In addition, since the cap portion 2 and the case main body 3 are hard, the urging springs 9 of the cap portion 2 mounted on the opening end 4 of the case main body 3 serve to positively push the liquid 6 contained in the case main body 3. That is, as shown in FIG. 9, in an initial stage of use, the liquid 6 contained in the tapered cylindrical portion 3a of the case main body 3 can be urged by urging the applying member 8 in the direction indicated by the arrow B in FIG. 9 and supplied to outside via the applying member 8 exposed from one side of the case main body 3.

The opening means 11 (i.e., a separable connecting means) serves to open the case 5. That is, a user holds the cap portion 2 and the tapered and straight cylindrical portions 3a and 3b of the case main body 3 of the case 5 with both hands, and puts fingers of both hands on both sides of the opening means 11. Thereafter, the user applies a force on the fingers to bend the case main body 3 at the position of the opening means 11 to tear off the thin circumferential wall of the opening means 11 from its one side, thereby separating the straight cylindrical portion 3b from the tapered cylindrical portion 3a (FIG. 12).

A portion of the applying member 8 is exposed at the tapered cylindrical portion 3a side from the straight cylindrical portion 3b removed upon opening of the case 5. As shown in FIG. 13, the substantially rhombic distal end face 7 of the applying member 8 has a shape suitable for applying a liquid on a wide affected part. That is, when the exposed substantially rhombic distal end face 7 of the applying member 8 is moved in the direction indicated by the arrow A in FIG. 13, a liquid can be applied on a wide affected part by the distal end face 7 of the applying member 8. In addition, when the distal end face 7 of the applying member 8 is moved in a direction indicated by an arrow E shown in FIG. 13, the distal end face can serve as a tip portion of a brush. Therefore, the applying member 8 can also apply a liquid on a narrow affected part. Since the liquid 6 is sealed in the tapered cylindrical portion 3a housing the applying member 8, the applying member 8 is wet with the liquid 6 in this state. Therefore, a desired portion can be applied or cleaned with the liquid 6.

Since the distal end portion of the straight cylindrical portion 3b to be separated upon opening is hollow (FIGS. 8 and 9), this distal end portion of the straight cylindrical portion 3b can be used as a cap to be fitted on the tapered cylindrical portion 3a. Therefore, the liquid applicator can be used a plurality of times (FIG. 11). FIG. 14 is a partially cutaway longitudinal sectional view showing a liquid applicator according to the second embodiment of the present invention corresponding to FIG. 8 of the first embodiment. FIGS. 15 to 17 are to side views taken along lines XV—XV, XVI—XVI, and XVII—XVII in FIG. 14. The second embodiment basically has the same structure as that of the first embodiment except for a difference to be described below. Therefore, the same reference numerals as in the first embodiment denote the same parts and a detailed description thereof will be omitted. In the second embodiment, the cross sectional shape of each of an applying member 8 and an opening means 11 is not rhombic but substantially elliptic. This embodiment has been made in consideration of ease in opening of a case main body 3. As shown in FIG. 15, the applying member 8 is an elliptic column, and its cross sectional shape (the same as the shape of a distal end face 7) is formed such that a thickness $\alpha 1$ in one direction of the applying member 8 is larger than a thickness $\beta 1$ in a direction perpendicular to the first direction. Therefore, also in the second embodiment, when the applying member 8 is moved in a direction indicated by an arrow A shown in FIG. 13, a liquid 6 can be applied on a wide area of an affected part by one application action.

As shown in FIG. 16, the shape of the opening means is substantially elliptic. In terms of moldability of the case main body 3, the cross sectional shapes of the reduced size transition portions 15 and 17 (see also FIG. 14) of the case main body 3 near the two sides of the opening means 11 are formed to be substantially elliptic as shown in FIGS. 15 and 17, respectively. An outer appearance of the other portion of the case main body 3 is substantially rhombic as in the first embodiment. As in the first embodiment, the thickness of the circumferential wall of a straight cylindrical portion 3b of the opening means 11 is as small as 0.05 to 0.5 mm, and preferably, 0.1 to 0.2 mm.

In the elliptic shape of the opening means 11, a ratio ($\alpha 0/\beta 0$) of a major axis $\alpha 0$ to a minor axis $\beta 0$ shown in FIG. 16 is preferably 3 to 1.2. If the ratio exceeds 3, the opening means 11 cannot be easily broken. If the ratio does not reach 1.2, although the opening means 11 can be easily broken, it is difficult to selectively use a surface for applying on a wide area and that for applying on a narrow area in the applying member 8 having a shape corresponding to that of the opening means 11. Note that the substantially elliptic shape includes an egg-like shape.

Since the sectional shape of the opening means 11 is substantially elliptic, no straight portion is present in the cross section unlike in a rhombus, i.e., the entire section is a curve. Therefore, when the opening means 11 is to be broken by an external force, a portion of the opening means 11 at which the external force is concentrated cracks, and the external force is constantly concentrated at the breaking portion. Therefore, breaking rapidly progresses to finally, completely open the opening means 11. If the sectional shape of the opening means 11 is rhombic, however, an external force is applied on straight portions in the cross section. Therefore, since the external force is dispersed by the straight portions, it is difficult to concentrate the force at one point. Even when the opening means 11 is broken and cracks, since the external force is not easily concentrated at the breaking portion, breaking does not easily progress. Therefore, nonseparated portions of the opening means 11 easily remain to make it difficult to open the opening means 11.

In order to use the distal end portion of the straight cylindrical portion 3b to be separated upon opening as a cap to be fitted on a tapered cylindrical portion 3a, a hollow portion inside the distal end of the straight cylindrical portion 3b is formed to be elliptic similar to a reduced size or neck portion 15 of the case. Therefore, since the distal end portion of the straight cylindrical portion 3b can be used as a cap in the same manner as that shown in FIG. 11 of the first embodiment, the liquid applicator of the second embodiment can be used a plurality of times.

The operation and the assembly method of the second embodiment except for those described above are exactly the same as those of the first embodiment.

The elliptic cross sectional shape of the opening means 11 can be adopted even when the shape of the distal end face 7 of the applying member 8 is not elliptic but another shape, e.g., rhombic or rectangular. Note that even if the distal end shape is not elliptic, the applying member 8 preferably has an elliptic shape substantially the same as that of the opening means 11 at a position adjacent to the opening means 11. In this case, therefore, another shape of the distal end face of the applying member 8, e.g., a rhombus is gradually changed into an ellipse toward the opening means 11.

Although a disinfectant solution is contained as the liquid 6 in the above two embodiments, the present invention is not limited to the above embodiments. For example, a toilet lotion or cleaning solution used in daily living can be arbitrarily contained as the liquid 6 in the case 5 of the liquid applicator 1.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A liquid applicator comprising:
   a case comprising a main body, a detachable portion, and separable connecting means formed therebetween, said connecting means including a reduced thickness portion of said case, and said connecting means having outer and inner surfaces having elliptical cross sections;
   a first handle grip having a polygonal cross section, formed as a part of said main body;
   defining means for defining a space for containing liquid in said main body;
   liquid contained in said space;
   a column liquid applying member in said case, and being arranged substantially close to an inner side surface of said main body so that said liquid applying member is secured by said main body, said liquid applying member extending into said detachable portion, and wherein said liquid applying member is made of liquid-holding material and is supplied with said liquid from said space; and
   a distal end surface on said liquid applying member, on which said liquid is applied, said distal end surface being longer in one direction than in another direction which is perpendicular to said one direction.

2. The liquid applicator of claim 1, further comprising a first reduced size neck portion having outer and inner surfaces having elliptical cross sections, said first reduced size neck portion being formed on said main body between said connecting means and said first handle grip.

3. The liquid applicator of claim 2, wherein said detachable portion comprises a hollow engaging portion formed at an end thereof, so that said detachable portion services as a cap which is engageable with said first reduced size neck portion after said case is broken along said separable connecting means.

4. The liquid applicator of claim 3, comprising a second grip formed as a part of said detachable portion, said second grip having an outer surface having a polygonal cross section.

5. The liquid applicator of claim 4, further comprising a second reduced size neck portion formed on said detachable portion between said connecting means and said second grip, said second reduced size neck portion having outer and inner surfaces having elliptical cross sections.

6. The liquid applicator of claim 5, wherein said polygonal cross sections of said first handle grip and of said second grip are rhomboid, and wherein said polygonal cross section of said first handle grip is substantially the same as that of said polygonal cross section of said second grip.

7. The liquid applicator of claim 1, wherein said elliptical cross section of the inner surface of said separable connecting means has long and short axes, the ratio therebetween said long and short axes being in the range of approximately 3 to 1.2.

8. The liquid applicator of claim 1, wherein said liquid applying member is substantially close to the inner side surfaces of said main body and of said detachable portion.

9. The liquid applicator of claim 1, wherein said distal end surface of said liquid applying member has said length in said one direction and said length in said another direction such that they have a ratio of approximately 3 to 1.2

10. The liquid applicator of claim 9, wherein said distal end surface of said liquid applying member is rhomboid-shaped.

11. The liquid applicator of claim 9, wherein said distal end surface of said liquid applying member is elliptical-shaped.

12. The liquid applicator of claim 1, wherein said distal end surface of said liquid applying member extends into said detachable portion while said detachable portion is attached to said main body.

13. The liquid applicator of claim 1, further comprising an urging spring and a plate provided in said space for containing said liquid, said urging spring being supported by said main body portion such that said urging spring extends in the axial direction of said column liquid applying member, and said plate being fixed to an end of said urging spring and being in contact with a proximal end surface of said liquid applying member.

14. The liquid applicator of claim 13, wherein said plate has a hole therein through which said liquid passes.

15. A liquid applicator comprising:
a case comprising a main body portion, a detachable portion, and separable connecting means formed therebetween, said connecting means including a reduced thickness portion of said case, and said connecting means having outer and inner surfaces having elliptical cross sections;
a first handle grip having a rhomboid-shaped cross-section, and formed as a part of said main body;
a hollow engaging portion formed at an end of said detachable portion, said detachable portion serving as a cap which is engageable, via said hollow engaging portion, with said main body after said case is broken along said separable connecting means;
a second grip o said detachable portion, and having an outer surface having a rhomboid-shaped cross-section which is substantially the same as the rhomboid-shaped cross section of said first grip;
defining means for defining a space for containing liquid in said main body;
liquid contained in said space;
a column liquid applying member in said case, and being arranged substantially close to an inner side surface of said main body so that said main body secures said liquid applying member, said liquid applying member extending into said detachable portion, and wherein said liquid applying member is made of liquid-holding material and is supplied with said liquid from said space; and
a distal end surface on said liquid applying member, on which said liquid is applied, said distal end surface being longer in one direction than in another direction which is perpendicular to said one direction.

16. The liquid applicator of claim 15, further comprising an urging spring and a plate provided in said space for containing said liquid, said urging spring being supported by said main body portion such that said urging spring extends in the axial direction of said column liquid applying member, and said plate being fixed to an end of said urging spring and being in contact with a proximal end surface of said liquid applying member.

17. The liquid applicator of claim 16, wherein said plate has a hole therein through which said liquid passes.

18. The liquid applicator of claim 15, wherein a side wall of said main body is slanted relative to the lengthwise direction of said main body, such that said main body is constricted toward said separation means, and said liquid applying member is held by a constructed portion of said main body.

19. The liquid applicator of claim 15, further comprising:
a first reduced size neck portion between said connecting means and said first handle grip; and
a second reduced size neck portion between said connecting means and said second grip;
said first neck portion having outer and inner surfaces which respectively have elliptical cross sections which are substantially the same as those of said second neck portion.

20. The liquid applicator of claim 15, wherein:
the elliptical cross section of the inner surface of said connecting means has long and short axes, a ratio therebetween being approximately 3 to 1.2; and
the distal end surface of said liquid applying member has said length in said one direction of said length in said another direction with a ratio therebetween of approximately 3 and 1.2.

21. The liquid applicator of claim 15, wherein said liquid applying member is substantially close to inner side surfaces of said main body and said detachable portion.

* * * * *